(12) United States Patent
Chatain et al.

(10) Patent No.: US 10,507,050 B2
(45) Date of Patent: Dec. 17, 2019

(54) PLATE FOR OSTEOSYNTHESIS

(75) Inventors: Frederic Chatain, Bernin (FR);
Stephane Denjean, La Roche (FR);
Thierry Gaillard, Lyons (FR);
Jean-Luc Delalande, Saint-Denis en Val (FR); Herve Chavane, Caluire (FR); Jean-Paul Carret, Lyons (FR);
Jacques Bejui, Paris (FR); Olivier Guyen, Lyons (FR); Olivier Tayot, Caluire (FR); Vincent Pibarot, Vienne (FR); Guillaume Derouet, La Turballe (FR); Benoit Gayraud, Le Loroux-Bottereau (FR)

(73) Assignee: NEOSTEO, Reze (FR)

( * ) Notice: Subject to any disclaimer, the term of this patent is extended or adjusted under 35 U.S.C. 154(b) by 1005 days.

(21) Appl. No.: 14/008,822

(22) PCT Filed: Mar. 27, 2012

(86) PCT No.: PCT/FR2012/050634
§ 371 (c)(1),
(2), (4) Date: Oct. 24, 2013

(87) PCT Pub. No.: WO2012/131246
PCT Pub. Date: Oct. 4, 2012

(65) Prior Publication Data
US 2014/0039498 A1 Feb. 6, 2014

(30) Foreign Application Priority Data
Mar. 29, 2011 (FR) .................................. 11 52601

(51) Int. Cl.
*A61B 17/80* (2006.01)

(52) U.S. Cl.
CPC ...... *A61B 17/8052* (2013.01); *A61B 17/8095* (2013.01); *A61B 17/8028* (2013.01); *A61B 17/8057* (2013.01); *A61B 17/8061* (2013.01)

(58) Field of Classification Search
CPC . A61B 17/80; A61B 17/8052; A61B 17/8057; A61B 17/8061; A61B 17/8095
(Continued)

(56) References Cited

U.S. PATENT DOCUMENTS

| 5,810,823 A | 9/1998 | Klaue et al. |
| 6,623,486 B1 | 9/2003 | Weaver et al. |

(Continued)

OTHER PUBLICATIONS

International Search Report, dated Jun. 19, 2012, from corresponding PCT application.

*Primary Examiner* — Si Ming Ku
(74) *Attorney, Agent, or Firm* — Ipsilon USA, LLP (57) ABSTRACT

A T-shaped plate for osteosynthesis, has at least three first attachment holes (124) and second attachment holes (113) including a curved linkage area (13). The epiphysis portion has a recess (34) with a curved profile from one end to the other of the T-bar when viewed from the top, and a curved profile when viewed from the side, and the diaphysis portion is straight and rigid. The plate is non-deformable at normal temperatures. The leg of the T has a rounded inner surface (56). The linkage area (13) has an S-shaped longitudinal cross-section, the ends (132, 133) of which that are adjoined with the bar and leg of the T, respectively, are substantially parallel to one another.

12 Claims, 4 Drawing Sheets

(58) Field of Classification Search
USPC .............. 606/280–299, 70, 71, 902–906
See application file for complete search history.

(56) References Cited

U.S. PATENT DOCUMENTS

| | | | |
|---|---|---|---|
| 2002/0065516 A1 | 5/2002 | Winquist et al. | |
| 2004/0127901 A1* | 7/2004 | Huebner | A61B 17/8042 606/281 |
| 2006/0015102 A1* | 1/2006 | Toullec | A61B 17/8061 606/86 B |
| 2008/0195157 A1 | 8/2008 | Orschler et al. | |
| 2008/0300637 A1* | 12/2008 | Austin | A61B 17/74 606/290 |
| 2010/0030277 A1* | 2/2010 | Haidukewych | A61B 17/8061 606/286 |
| 2013/0165979 A1* | 6/2013 | Greenberg | A61B 17/8061 606/281 |

* cited by examiner

PLATE FOR OSTEOSYNTHESIS

BACKGROUND

Field of the Invention

The invention relates to an osteosynthesis plate.

It also relates to a device and a method using such a plate which is to be applied to at least part of a bone.

This type of plate is not only intended to come into direct contact with the bone (by contrast to the plates which are used to bring together or even compress two bone fragments, by way of fixation screws or rods, and which are therefore not necessarily in contact with the bone) but can also have a shape corresponding at least partially to the external shape of the bone.

It has an application particularly but not exclusively in the field of design and production of osteosynthesis equipment and, more precisely, of plates intended to be connected to and in contact with a long bone at several points thereof.

A plate within the field of the invention can be used in particular in an osteotomy operation, the aim of which may be, for example, to modify the structure of a supporting bone, so as to relieve a joint or a worn part.

Thus, during an open osteotomy, a surgeon makes a partial cut in a bone (tibia and femur in particular), then inserts a wedge into the resulting notch, in order to open the bone by pivoting the two bone parts delimited by the notch through a previously defined angle (generally between 6 and 14°).

When the desired angle is reached, he connects a plate from the field of the invention to the two bone parts delimited by the notch, in order to fix their spacing. It will be noted that a plate used in the case of an open osteotomy is called an addition plate.

Generally, the plate is connected to the bone by means of screws or threaded rods.

Natural ossification then allows the bone to regenerate within the resulting notch, during a period of the order of several months during which the plate remains fixed to the bone of the patient, in order to stabilize the bones and prevent excessive mobility between the fragments.

When it has completely regenerated, the bone is sufficiently stable for the plate to be able to be removed from the body of the patient.

Similarly, a plate within the field of the invention can be used to connect the two bone parts separated by the cut made in the case of a closed osteotomy, which differs from an open osteotomy in that the partial cut made in the bone defines a beveled wedge intended to be removed. In the case of a closed osteotomy, such a plate is called a subtraction plate.

In fact, the invention relates more particularly to plates intended to be used on a long bone, that is to say a bone of which the longitudinal dimensions are much greater than its other dimensions.

Such bones are characterized by the fact that they have:
two distal portions called epiphyses;
a central portion called the diaphysis;
two intermediate portions situated between the diaphysis and each of the epiphyses and called the metaphyses.

Thus, during an osteotomy, the bone is generally cut in the area of a metaphysis of a long bone, and a plate is then connected, on the one hand, to the epiphysis and, on the other hand, to the diaphysis surrounding this metaphysis.

For this, the plate can be divided into a foot in the lower part intended to be connected to the diaphysis, and head surmounting the foot in the upper part and intended to be connected to the epiphysis.

In addition, the plate when fitted generally has a profile similar to the external shape of the bone, particularly in the area of its epiphysis portion, such that it comes to bear on this portion. Once the plate is connected to the bone at the various points provided, this makes it possible to reduce the potential mobility associated with the play that may possibly appear in the long term and thus contributes to reinforcing the hold and stability of the plate on the bone.

Description of the Related Art

According to the prior art, the osteosynthesis plates belonging to the field of the invention are distinguished by their being able to be deformed or being unable to be deformed by a surgeon during an operation.

Thus, a plate that is deformable at ambient temperature is able to be deformed by the surgeon, generally by means of a manual tool, so as to try to give the plate a shape that is as close as possible to the external shape of the bone.

A deformable plate of this kind is generally made of a metallic material such as stainless steel, machined flat and then folded.

However, the use of a deformable plate has its limitations, for several reasons, among which:
the adaptation of the plate to the shape of the bone is difficult and depends on the skill and experience of the surgeon;
the deformation of a plate is more difficult, or even impossible, in certain directions, especially in the case of plates having a small width;
the deformation of the plate supposes the use of additional tools during an operation, hence their prior sterilization;
the operation of deforming the plate and then placing the deformed plate on the bone often has to be repeated several times by the surgeon before he proceeds to fix it, which causes a loss of time and needlessly prolongs the period of anesthesia of the patient;
the deformations made to the plate have a tendency to weaken it or even instigate breaks.

By contrast, a plate that is non-deformable at ambient temperature makes it possible to eliminate a number of these disadvantages.

Such a plate is in fact ready to use and can be much stronger, since it is not weakened by deformations performed during an operation.

However, a non-deformable plate according to the existing techniques generally has, in its head part intended to be connected to the epiphysis, a shape that may correspond to a portion of a cylinder.

Thus, the head of the plate, when viewed from above, can have a continuously curved profile, whereas it has a straight profile when viewed from the side.

However, the shape of the bone and in particular of the epiphysis is not straight but generally inwardly curved, when viewed from the side and also from above.

When he fits a non-deformable plate on the bone, there is a good chance of the surgeon having to fix it in a position in which it does not bear satisfactorily on the epiphysis, since the cylindrical shape of the head considerably limits the possibilities the surgeon has to adjust the position of the plate.

Even by moving it slightly around the epiphysis until reaching three points of contact between the plate and the bone, he increases the space taken up by the plate above the bone.

Plates are also known (US2008/0300637) which combine polyaxial fixation with a contour that adapts better to the bone. Such plates, which can be made of all types of materials, are quite thin and flexible in order to match the shape of the bone.

However, they require numerous screws in different directions and are not easy to use.

OBJECTS AND SUMMARY

The object of the invention is in particular to overcome these disadvantages of the prior art.

More specifically, the object of the invention is in particular to make available a rigid and non-deformable osteosynthesis plate of which the congruence to a part of the bone is independent of the operation decided on by the surgeon.

The invention particularly permits good congruence on the epiphysis portion in the case of a use as an addition plate and as a subtraction plate, while at the same time being easy to manipulate and fix.

On account of the rigidity of the plate, the invention accepts not having contact over the whole bone, even though experience shows that a plate which is poorly adjusted and/or protrudes too much above the bone causes the patient to experience pain.

However, by virtue in particular of the good congruence in the area of the epiphysis involved, the results obtained with the plate according to the invention surprisingly prove to be perfectly acceptable and satisfactory.

The invention also has the object of making available an osteosynthesis plate of this kind that can be compatible with a large number of bones of similar shapes and dimensions.

Another object of the invention is to make available a plate of this kind that does not cause the patient pain.

The invention also relates to the production of a strong plate.

To this end, and in order to achieve these objects and also others that will become apparent below, the present invention proposes in particular an osteosynthesis plate shaped as a T and symmetrical with respect to a longitudinal axis, having an epiphysis portion (head) that forms the bar of the T and is provided with at least three first fixation holes for first anchoring screws, and a diaphysis portion (foot) that forms the leg of the T and is provided with second fixation holes for second anchoring screws and is connected to the epiphysis portion by a curved joining area, the epiphysis portion having a concavity with a curved profile from one end to the other of the bar of the T when viewed from above, and a curved profile when viewed from the side, the diaphysis portion being straight and rigid, characterized in that said plate is non-deformable at normal temperatures, in that its diaphysis portion has an inner surface that can be directed toward the bone and that has a convex shape, and in that the joining area has an S-shaped longitudinal cross section, of which the ends joining respectively to the bar and to the leg of the T are substantially parallel to each other.

Normal temperature means a temperature of between −20° C. and +50° C., and in particular the ambient temperature of between 10° C. and 35° C., advantageously of between 20° C. and 30° C.

Concavity means the inner surface of concave shape of the part or area concerned.

Joining ends that are substantially parallel mean ends that have substantially parallel inner surfaces, that is to say forming an angle of between 0° and 1 to 5°, advantageously between 0 and 2°, for example less than 1°.

Convex surface means a surface which, in cross section, has a profile which is at least partially convex toward the bone on which the plate is to be fixed. This convexity is obtained, for example, by a circular or elliptic segment with a height (relative to the chord) of less than 0.5 mm, for example of 0.2 mm.

The invention thus proposes in particular an osteosynthesis plate which is made of a material non-deformable at ambient temperature and is able to be connected to an epiphysis and to the diaphysis of a long bone, said plate comprising the leg of the T or foot in the lower part and the bar of the T or head in the upper part, provided with a first distal end and second distal end, said head being intended to be connected to the epiphysis and the foot to the diaphysis, said head having, when viewed from above, a continuously curved profile from its first distal end to its second distal end and, when viewed from the side and at least in one cross section passing through the foot, a continuously curved profile along the full extent of said head.

Thus, the plate first of all has the advantages associated with the fact that it is non-deformable during the operation: it is ready for use, and it is never adapted before being fixed to a bone, which allows it to retain its mechanical properties and simplifies the operation performed by the surgeon.

In addition, the curved profiles presented by the head of the plate, both when viewed from above and viewed from the side, give it an enveloping shape that improves its capacity to be congruent to the epiphysis portion of the bone for which it is intended.

In particular, the curvatures of the plate allow the surgeon to adjust the position of the plate on the bone, by sliding the plate a greater or lesser distance from the diaphysis of the bone, but applying it to the maximum extent on the epiphysis of the bone, and this irrespective of the desired use, that is to say as an addition plate with upward movement of the epiphysis of the bone, or as a subtraction plate with lowering of the epiphysis.

This adjustment, with which it is necessary to accept leaving a space between the foot of the T and the diaphysis portion (and therefore not having optimal congruence over the entire bone), is possible by virtue of the fact that the head of the plate can be moved in the manner of a ball joint with respect to the epiphysis.

The curved shapes of the head of the plate make it possible in fact to minimize the invasive aspect of the latter in the body of the patient and, in a manner that proves acceptable, reduce the risk of onset of pain in the patient.

Presenting a T shape when viewed from the front, said plate is perfectly designed to be connected to the bone isostatically, hence in a stable manner, in three contact areas of the bone, of which two in the epiphysis and the third in the diaphysis.

Such a plate, in particular as an addition plate, is symmetrical and can therefore be equally applied, with the same advantages, on two symmetrical bones of, respectively, a left limb and a right limb of the patient. This feature improves the compatibility of the plate, which is able to fit a greater number of bones. The number of different plates that have to be produced, and that the surgeon needs to have available, is also reduced.

The plate according to the embodiment of the invention more particularly described here has a convex surface on the inner face of its foot, which also allows the sliding and positioning on the diaphysis of the bone that is to be repaired, in combination with the curvatures of the head.

Finally, the S-shaped joining area, with parallel ends in this embodiment, further facilitates and permits the high degree of modularity of the plate, resulting in excellent ease of use by the surgeon. Again it was necessary to accept fixation on the bone at only three points in some applications. However, experience has shown that this result was entirely satisfactory and that the patient did not experience any pain as a consequence.

In one advantageous embodiment, the concavity has an inner surface in the shape of a portion of an ellipsoid of revolution about an axis of revolution situated in the plane (P) of symmetry of the longitudinal axis.

Advantageously, the curved profile of the head, when viewed from the side, has a constant radius of curvature R1.

This feature means that the plate can have a very regular shape, which facilitates its adjustment on the epiphysis and reinforces its compatibility with bones of similar shapes and dimensions.

Added to the regularity of the curved profile of the head when viewed from above, it makes it possible to obtain an ovoid shape, even a spherical shape, which optimizes the enveloping qualities of the plate with respect to the epiphysis of the bone.

Also advantageously, the axis of revolution of the inner surface of the epiphysis portion forms, with the leg of the T of the diaphysis portion, a re-entrant angle γ of between 5° and 45°, for example of between 10 and 30°, for example of 20°.

Re-entrant angle means an angle directed toward the inside of the bones in relation to the longitudinal axis of the leg of the T.

In advantageous embodiments, one or more of the following provisions are also made:
the value of the constant radius of curvature R1 is between 20 mm and 40 mm, for example 32 mm (in the case of an addition plate, which can be used in an open osteotomy) or 22.5 mm (in the case of a subtraction plate, which can be used in a closed osteotomy).
These values give the plate a shape that adapts perfectly to most of the bones on which it is able to be fitted, such as tibias and femurs;
the foot has an upper joining part belonging to the S-shaped area joining to the head and, when viewed from the side and in a cross section passing through said foot, has a continuously curved profile.

In other words, the S-shaped joining area has, in longitudinal cross section, a radius of curvature R2 in its concave part.

Thus, the plate has a shape that better follows the general curvature of the bone, from the epiphysis to the diaphysis by way of the metaphysis. Its congruence to the bone is thus improved for this reason;
the radius of curvature R2 of the continuously curved profile of said upper joining part when viewed from the side is constant and has a value of between 15 mm and 40 mm, for example 20 mm (in the case of an addition plate, which can be used in an open osteotomy) or 22.5 mm (in the case of a subtraction plate, which can be used in a closed osteotomy).

Here too, these values give the plate a shape that adapts optimally to most of the bones on which it is able to be fitted.

With the head comprising at least two first holes or orifices intended to be passed through by a screw in order to connect the plate to the epiphysis, and with the foot comprising at least one second hole or orifice intended to be passed through by a screw for connecting the plate to the diaphysis, it is possible to achieve a simple, rapid and stable fixation of the plate to the bone with a minimum number of screws.

It is thus possible to obtain optimal fixation of the plate in the area of the epiphysis of the bone, at two points which can be spaced apart from each other to the maximum extent in order to avoid mobility of the plate along the median axis between these two points.

The fixation of the plate at a third point situated in the area of the diaphysis, by a screw able to pass through the foot at a position very far from the head, thus allows the plate to be held in place and minimizes the risk of its having any play, which in the long term causes instability, through a sort of tripod effect.

Although a greater number of screws passing through the plate, in particular three screws in the head and three screws in the foot, can also improve the hold of the plate on the bone, since it increases the probability of a screw being present very close to the different points of contact between the plate and the bone, the present invention does not require them;
the osteosynthesis plate is made of a material comprising titanium.

Titanium is able to give the plate significant advantages in terms of strength, durability, and safety for the patient.

The invention also makes available a device having a plate of the kind described above, characterized in that the plate has two first lateral holes, which are each provided with a seat and with a thread cooperating with a corresponding screw,
in that it has the two corresponding lateral screws which, when screwed into said first lateral holes, form a first angle with the inner surface of the epiphysis portion,
in that the plate has a first central hole, which is provided with a seat and with a thread cooperating with a corresponding central screw, and
in that it has the corresponding central screw which forms a second angle with the inner surface of the epiphysis portion.

Advantageously, the difference between the first angle and the second angle is between 1° and 5°.

In one advantageous embodiment, the first screws are threaded along only part of their length and are convergent and self-locking.

This self-locking is effected in a manner known per se.

The invention also makes available a method for fitting a plate for reduction of a distal fracture of a long bone, in which method, with the plate being shaped as a T and symmetrical with respect to a longitudinal axis, having an epiphysis portion that forms the bar of the T and is provided with at least three first fixation holes for first anchoring screws, and a diaphysis portion that forms the leg of the T and is provided with second fixation holes for second anchoring screws and is connected to the epiphysis portion by a curved joining area, the epiphysis portion having a concavity with a continuously curved profile from one end to the other of the bar of the T, and a continuously curved profile when viewed from the side, the diaphysis portion being straight and rigid,
characterized in that
the plate is placed on the long bone to be repaired, after the two bone parts have first of all been spaced apart or brought closer together, by a defined chosen angle of between 5° and 14°, and have been blocked relative to each other with or without insertion of an insertion element, the plate is then moved by sliding it in order to find the maximum congruence between the plate and the bone, the shape of the epiphysis portion and the rigidity of the plate allowing the latter to be slid and positioned manually, in such a way that two contact points at least are obtained with respect to the first end holes of the bar, on the fractured epiphysis portion, and one contact point is obtained on the diaphysis portion, once the position of congruence has been obtained by contact with these two points, the bar of the T on the one hand is fixed at its ends at these two points, by screwing and locking a screw respectively in the two first corresponding holes on the fractured distal portion of the bone, and, said plate being non-deformable at normal temperatures and its diaphysis portion having an inner surface able to be directed toward the bone and of convex shape, one also on the other hand fixes the branch of the T on the side of its convex part by screwing a screw into the second hole coming into contact with the proximal part of the bone, such that the plate is thereby fixed without compression at three points of the bone that is to be repaired.

BRIEF DESCRIPTION OF THE DRAWINGS

Other features and advantages of the invention will become clearer from reading the following description of embodiments of the invention, which are given as illustrative and non-limiting examples and with reference to the accompanying drawings, in which.

DETAILED DESCRIPTION

As has been indicated above, one of the principles of the invention is to make available an osteosynthesis plate which is non-deformable at ambient temperature and which has a foot intended to be connected to the diaphysis of a bone and has a head intended to be connected to an epiphysis of the same bone, such that the head has a continuously curved profile, when viewed from above and also when viewed from the side, while permitting easy adjustment by virtue of the other features described hereinbelow.

Figure 1:
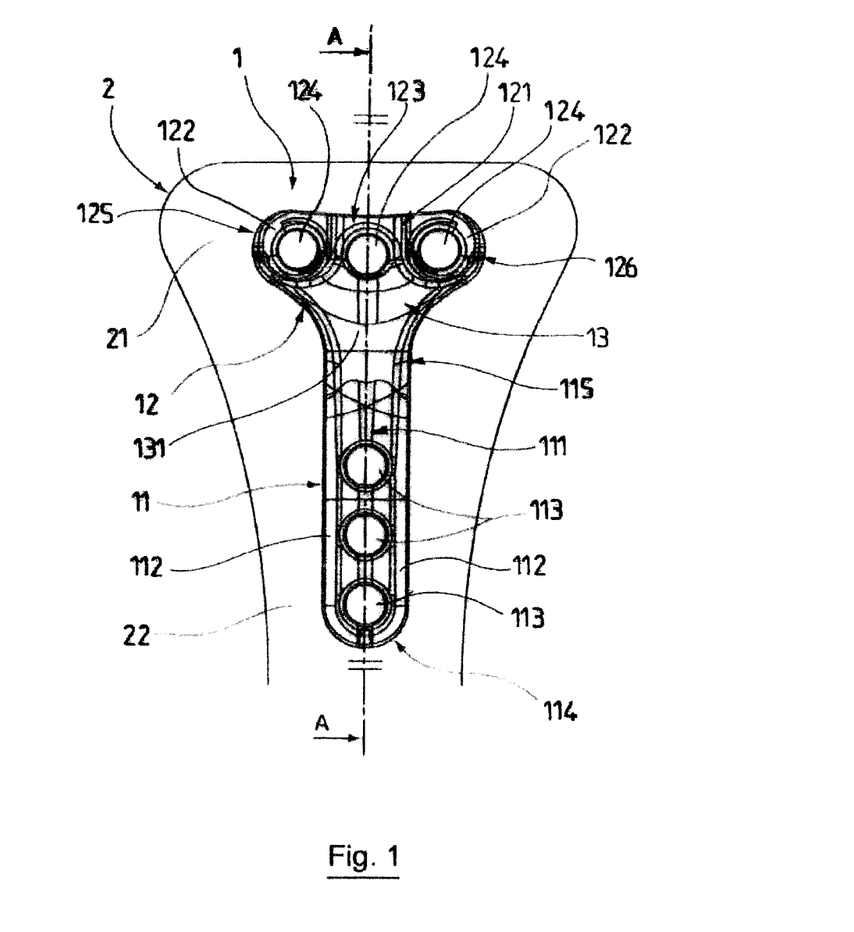
FIG. 1 is a front view of an osteosynthesis plate according to one embodiment of the invention.

Referring to FIG. 1, a plate 1 according to the invention is shown in front of a bone 2, on which it is intended to be fixed.

The bone 2 illustrated is a long bone, shown in part here, specifically in the area of one of its epiphyses 21 and as far as its diaphysis 22.

The plate 1 is rigid and non-deformable at ambient temperature. Thus, during an operation performed by a surgeon, it is connected to the bone 2 without undergoing deformation.

The plate 1 is made, for example, of a material comprising titanium, or of any other material allowing a good compromise between mechanical performance, ease of shaping, and cost.

In order to be non-deformable, such a plate 1 has a thickness of at least 2 mm. Intended for the field of osteosynthesis, it is characterized by a maximum thickness of the order of 4.5 mm.

In FIG. 1, the plate 1 is shown in a view from the front. It has the general shape of a T.

This view illustrates more precisely that the plate 1 is formed, in the lower part, by a foot 11 in the shape of a substantially rectangular blade with a thickness of 2 mm and with a plane surface 111, for example flat and with softening lateral bevels 112, its other surface (situated toward the bone) being convex, as will be described with reference to FIG. 6.

The plate has a head 12 located in the upper part and connected to the lower part by an S-shaped area 13, such that the plate 1 is symmetrical with respect to the longitudinal median plane of said foot, and it has a top 121 substantially parallel to the plane surface 111.

In the preferred embodiment illustrated, the plate has a T shape. Its head 12 is intended to be connected to the epiphysis 21, while its foot 11 is intended to be connected to the diaphysis 22.

The head 12, which surmounts the foot, comprises an upper surface 121 provided with two flat end recesses 122 and with a plane upper central part 123 in the continuation of the upper surface of the foot 11 and of that 131 of the joining area 13. The head comprises three threaded orifices 124 able to cooperate with fixation means, such as fixation screws or rods in particular (not shown).

More precisely, it comprises a first distal end 125 and a second distal end 126, between which the three orifices 124 are uniformly distributed, respectively on the flat areas 122 and the central part 123.

The plate 1 is thus intended more particularly to be connected to the epiphysis 21 by at least one screw passing through the head 12 and, preferably, by three screws passing through these orifices 124.

The foot 11 is provided with three threaded orifices 113 able to cooperate with fixation means similar to those indicated above. It extends between a rounded distal end 114, at the lower part, and an upper part 115 connecting it to the head 12.

The three orifices 113 are uniformly distributed, starting from the distal end 114 of the foot as far as, for example, the half-way point of the length of the foot. The plate 1 is intended to be connected to the diaphysis 22 by at least one screw passing through the foot 11 and, preferably, by three screws passing through these orifices 113 and self-locking in the threaded orifices.

Thus, the head 12 comprises at least one orifice 124 intended to be passed through by a screw in order to connect the plate to said epiphysis 21, and said foot 11 comprises at least one orifice 113 intended to be passed through by a screw in order to connect the plate to said diaphysis.

The ends 125 and 126 of the head 12 and the end 114 of the foot 11 can thus constitute bearing points of the plate 1 on the bone 2. These three points being eccentric to the maximum extent, they thereby guarantee a high degree of stability of the plate on the bone.

Figure 2:
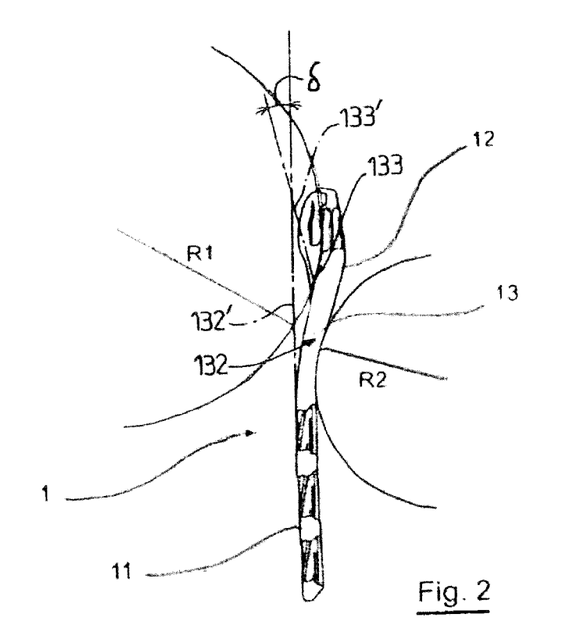
FIG. 2 is a cross-sectional side view along A-A of the plate from FIG. 1.
Figure 3:
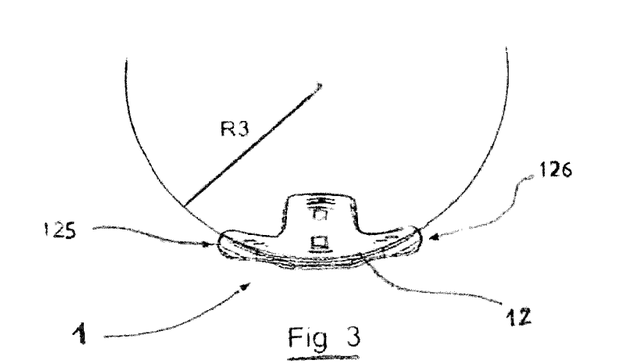
FIG. 3 is a top view of the plate from FIG. 1.

In FIG. 2, the plate 1 is shown in a side view, while in FIG. 3 its head 12 is shown in a top view, with reference to the front view illustrated in FIG. 1.

FIG. 3 shows that the head 12 has, in a top view, a profile that is continuously curved from its first distal end 125 to its second distal end 126.

This profile is characterized by a radius of curvature R3 which varies, such that the profile is substantially elliptic, but which could equally well also be constant, such that the segment shown has a circular shape.

Similarly, FIG. 2 illustrates the fact that the plate 1 has, in a side view and at least in a cross section passing through said foot 11, a profile that is continuously curved along the full extent of the head 12.

This continuously curved profile of the head 12, as viewed from the side, has a radius of curvature R1 which is constant.

The value of the radius of curvature R1 is between 20 mm and 40 mm.

According to a preferred embodiment of what is called an addition plate, this value is 32 mm. According to another preferred embodiment (not shown), of what is called a subtraction plate, this value is 22.5 mm.

In the same way, it will be noted that the head 12 of the plate 1 has a continuously curved profile along the full extent of the head, with a constant radius of curvature, in other cross-sectional views not passing through the foot 11.

In particular, the profile of the head 12 has the same radius of curvature R1 on the other vertical cross sections made between the two distal ends of the head (other cross sections not shown).

Thus, the head 12 has an ovoid shape, even a spherical shape, particularly suitable for allowing its adjustment on the epiphysis 21 of the bone for which it is intended.

FIG. 2 also illustrates that said upper part of said foot 11 belonging to the area of joining 13 to said head 12 has, in a side view and in a cross section passing through said foot 11, a continuously curved profile.

The radius of curvature R2 of said continuously curved profile of said upper joining portion 115, seen from the side, has a value of between 15 mm and 40 mm.

According to a preferred embodiment of what is called an addition plate, R2 has a value of 20 mm.

According to another preferred embodiment (not shown), of what is called a subtraction plate, R2 has a value of 22.5 mm.

By extension, the foot 11 has a curved profile with radius of curvature R2 across the entire width of the foot, in other words in all cross sections of the foot made parallel to the one shown in FIG. 2.

Thus, the plate 1 is congruent to the bone 2, from the epiphysis 21 to the diaphysis 22.

As can be seen from FIG. 2, the joining area has an S shape, of which the ends 132, 133 have plane or substantially plane longitudinal surfaces 132', 133' (hence also their longitudinal sections) which are substantially parallel or form an angle δ toward the inside, i.e. toward the bones, of between 0° and 5°, for example between 0° and 2°, for example 1°.

Figure 4A:
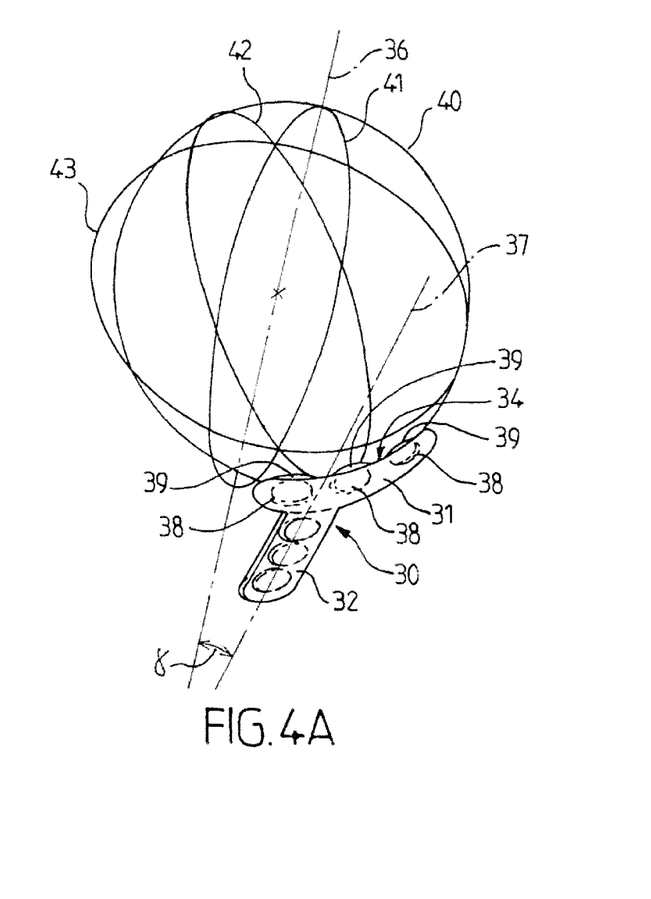
FIGS. 4A and 4B are perspective views of the plate from FIG. 1, in two positions serving to illustrate an embodiment of the shape of the concavity of the head of the plate according to the invention.
Figure 4B:
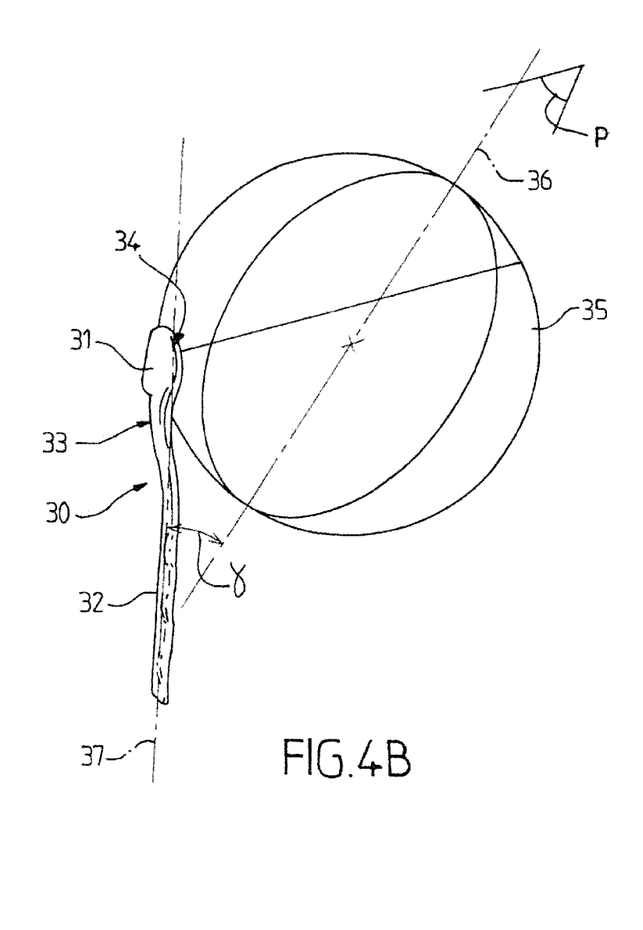

FIGS. 4A and 4B show a plate 30 according to one embodiment of the invention, comprising a curved head 31 and a straight foot 32 which are joined together by an S-shaped joining area 33.

The inner surface 34 of the cavity is in the shape of a portion of a sphere 35 of revolution about an axis of revolution 36 situated in the plane P of symmetry of the longitudinal axis 37 of the plate 30.

The axis of revolution 36 forms an angle γ of >0° with the longitudinal axis (or more generally the leg of the T), for example of 30°, such that the concavity of the inner surface 34 is directed toward the foot (downward).

In this embodiment, each hole 38 has, on its inner face, lips 39 in the upper part of the hole (cf. FIG. 4A) in the shape of a half or third of a crown, with a thickness of the order of 1 mm permitting better screwing (width of fixation), contact which if need be will be able to be inscribed in part on the meridians 40, 41, 42 of the sphere of diameter 43, for example.

Figure 5:
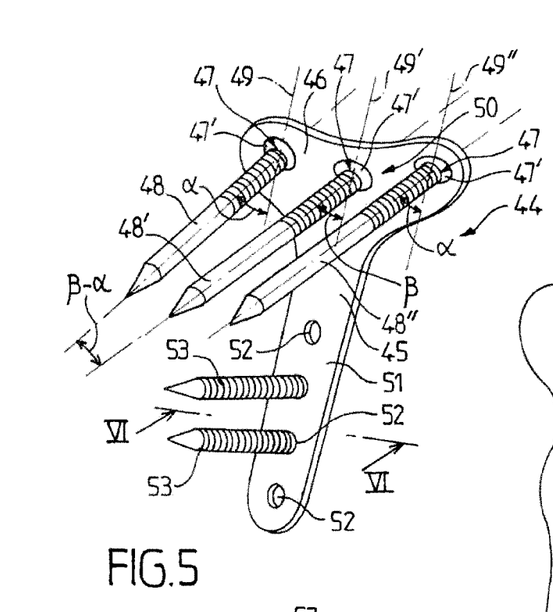
FIG. 5 is a perspective view of a device with a plate according to one embodiment of the invention.

FIG. 5 shows a device 44 comprising a plate 45 according to another embodiment of the invention, provided with a head 46 with three holes 47 provided with a seat in the form of a partial crown, for example in the form of a similar crescent of small thickness 47', and three screws 48, 48', 48" which are threaded along only part of their length near the screw head, for example on only a portion of their length, for example a third.

Once they have been screwed in, the screws 48 and 48", being lateral screws, form a first angle α with the tangent 49, 49', 49" to the inner surface 50, and the central screw 48' forms a second angle β, the difference between α and β being 3°, for example.

The plate 45 comprises a foot 51 provided with four uniformly distributed holes 52 and with at least two corresponding screws 53 threaded along substantially their entire length.

Figure 6:
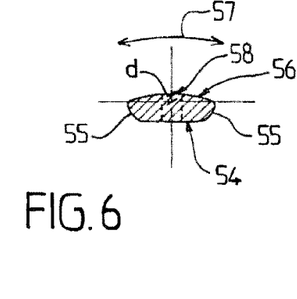
FIG. 6 is a cross-sectional view along VI-VI of the foot of the plate from FIG. 5.

Referring to FIG. 6, the foot has a substantially trapezoidal cross section with a flat upper face 54 and two lateral sides 55 in the form of rounded bevels, and a bone contact face 56 of convex shape, with a maximum thickness d of between 0.1 and 0.5 mm, for example of 0.2 mm.

This feature allows better adjustment of the plate on the diaphysis and epiphysis, allowing a slight pivoting (arrow 57) of the plate along the crest line 58 of the convex surface 56 during adjustment, and making it possible to ensure precision in the positioning of the point of contact with the foot (without interface of the rest of the foot).

FIGS. 7, 8, 9 and 10 show the function of a plate 60 of the type described with reference to FIG. 1.

Figures 7, 8, 9, 10:
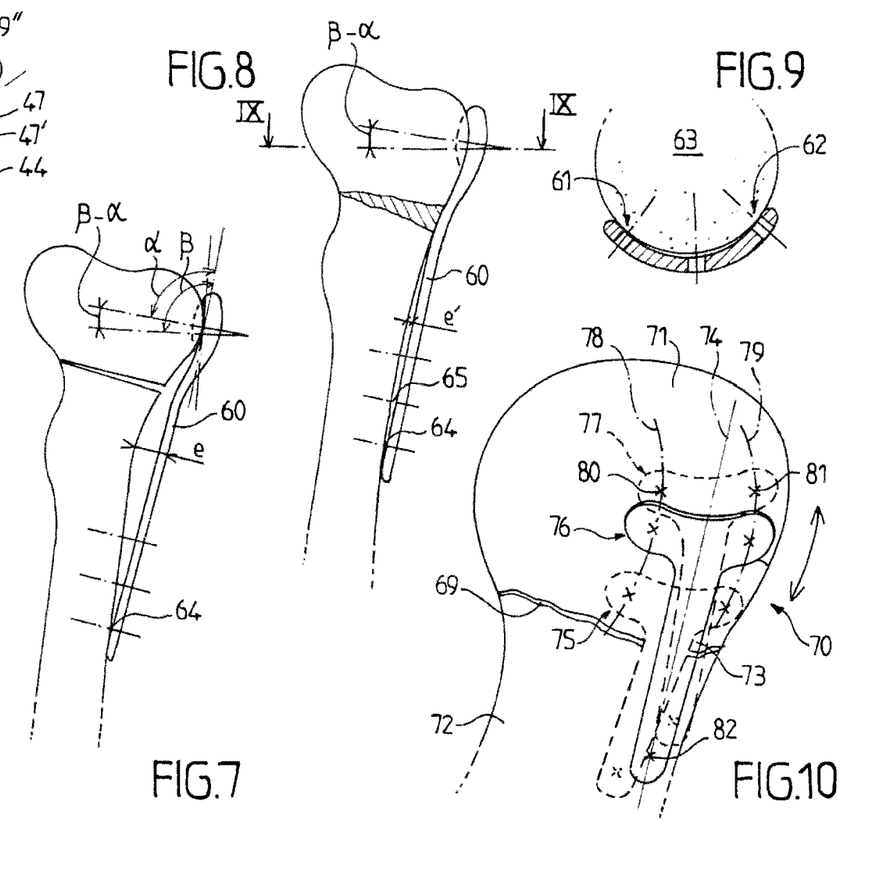
FIGS. 7 and 8 are side views illustrating the positioning of a plate according to the invention when used as a subtraction plate (FIG. 7) and as an addition plate (FIG. 8).
FIG. 9 is a schematic cross-sectional view along IX-IX of the plate from FIG. 8.
FIG. 10 is a schematic view showing the plate in several positions permitting optimized adjustment thereof.

FIG. 7 shows the plate 60 in the case where it is used as a subtraction plate.

In this case, it is in contact on at least two end points 61 and 62 (cf. FIG. 9) in the epiphysis portion 63 and on one point 64 of the diaphysis portion, quite a large space e (several mm) being able to exist between the rest of the foot of the plate and the bone.

FIG. 8 shows the same non-deformable plate 60 still in contact on the points 61 and 62 of the epiphysis portion, but by contrast in contact differently on one or two points 64, 65 of the diaphysis portion, with an almost zero space e' this time existing between the rest of the foot of the plate and the bone.

The use of a plate according to the invention will now be described with reference in particular to FIG. 10.

The surgeon who decides to apply a plate in order to repair a fracture 69 on a bone 70 comprising an epiphysis portion 71 and a diaphysis portion 72 frees this fractured part of the flesh and tendons and/or muscles around it, and he then prepares the operation by spreading the bone parts away from each other and sliding a wedge in between them, or, by contrast, bringing them together after having removed a slice of bone for example.

In order to reduce this fracture 69 and/or to fix it in position, he then applies the T-shaped plate 73 according to the type described with reference to the preceding figures.

The plate, being symmetrical with respect to its axis 74 and convex, will be able to be adjusted by slight lateral pivoting and is furthermore positioned, for optimization of its position, by sliding it between the positions 75, 76, 77 indicated in FIG. 10.

To do this, the surgeon moves the plate by sliding it in order to find the axial congruence between the plate and the bone along the curves 78, 79 in dot-and-dash lines in the figure.

He does this such that two contact points 80, 81 at least are obtained opposite the first end holes of the bar on the fractured epiphysis portion 71, and one point at least is obtained on the end of the leg of the T with the diaphysis portion.

Once the position of congruence has been obtained by contact with these two points, he fixes the bar of the T at these ends on these two points by carrying out screwing and locking, in a manner known per se, in the two corresponding first holes.

Since the plate is non-deformable, the part which had slid along the diaphysis portion is also fixed simultaneously and/or progressively and alternately with the screwing of the first screws, by way of at least one contact point 82 of the convex part, by screwing a screw into the second hole nearest the contact or centered on the contact point 82.

The plate is thus screwed without compression at three points of the bone to be repaired, making it possible to obtain excellent and lasting fixation.

Other embodiments, based on the principle of an osteosynthesis plate as has just been described, are of course conceivable without departing from the scope of the invention.

The invention claimed is:

1. An osteosynthesis T-shaped plate comprising:
an epiphysis portion that forms a bar of the T and is provided with at least three first fixation holes for first anchoring screws; and
a diaphysis portion that forms a leg of the T and is provided with second fixation holes for second anchoring screws,
wherein said epiphysis portion and said diaphysis portion are connected by a curved joining area,
wherein the epiphysis portion is concave, with a curved profile from one end to the other of the bar of the T, said concavity of said epiphysis portion of said plate being along an inner surface of said plate, said epiphysis portion also having a curved profile when viewed from a side,
wherein the diaphysis portion is straight and rigid, wherein said plate is titanium, and symmetrical with respect to a longitudinal axis,
and wherein said diaphysis portion is convex along said inner surface said convex inner surface of said diaphysis portion having a camber that, when viewed in a plan orthogonal to said longitudinal axis, is convex from a first longitudinal edge of the leg to a second longitudinal edge of the leg, said convex inner surface of said diaphysis portion being directed toward a bone, and
wherein said curved joining area has an S-shaped longitudinal cross section, such that ends of said curved joining area join respectively to the epiphysis portion and to the diaphysis portion of the T-shaped place in a manner substantially parallel to each other.

2. The osteosynthesis plate as claimed in claim 1, wherein the concave inner surface of the epiphysis portion is in the shape of a portion of an ellipsoid of revolution about an axis of revolution situated in a plane of symmetry of the longitudinal axis.

3. The plate as claimed in claim 2, wherein the ellipsoid is a sphere of radius R1.

4. The plate as claimed in claim 3, wherein the axis of revolution of said inner surface of the epiphysis portion forms, with the leg of the T of the diaphysis portion, a re-entrant angle γ of between 5° and 45°.

5. The plate as claimed in claim 2, wherein the axis of revolution of an inner surface of the epiphysis portion forms, with the leg of the T of the diaphysis portion, a re-entrant angle γ of between 5° and 45°.

6. The plate as claimed in claim 1, wherein the curved profile of the concave inner surface of the epiphysis portion, in a side view, is of constant radius.

7. The plate as claimed in claim 6, wherein the radius is between 20 mm and 40 mm.

8. The plate as claimed in claim 7, wherein the radius is equal to 32 mm, in order to form an addition plate.

9. The plate as claimed in claim 7, wherein the radius is equal to 22.5 mm, in order to form a subtraction plate.

10. The plate as claimed in claim 1, wherein the curved joining area has, in longitudinal cross section, a radius of curvature of between 15 mm and 40 mm in its concave part.

11. The plate as claimed in claim 10, wherein the radius of curvature is equal to 20 mm, in order to form an addition plate.

12. The plate as claimed in claim 10, wherein the radius of curvature is equal to 22.5 mm, in order to form a subtraction plate.

* * * * *